United States Patent
Bruederle

(10) Patent No.: US 11,058,597 B2
(45) Date of Patent: Jul. 13, 2021

(54) SAFE CONTROL METHOD AND SYSTEM

(71) Applicant: KARL STORZ SE & Co. KG, Tuttlingen (DE)

(72) Inventor: Klaus Bruederle, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 0 days.

(21) Appl. No.: 17/002,206

(22) Filed: Aug. 25, 2020

(65) Prior Publication Data
US 2021/0059884 A1    Mar. 4, 2021

(30) Foreign Application Priority Data

Aug. 26, 2019   (DE) .................... 10 2019 122 868.9

(51) Int. Cl.
| | |
|---|---|
| *G06F 3/048* | (2013.01) |
| *A61G 13/02* | (2006.01) |
| *G16H 40/63* | (2018.01) |
| *G06F 3/01* | (2006.01) |
| *G06F 3/0488* | (2013.01) |
| *G06F 21/36* | (2013.01) |

(52) U.S. Cl.
CPC ............ *A61G 13/02* (2013.01); *G06F 3/014* (2013.01); *G06F 3/0488* (2013.01); *G06F 3/04883* (2013.01); *G06F 21/36* (2013.01); *G16H 40/63* (2018.01); *A61G 2203/16* (2013.01)

(58) Field of Classification Search
CPC .... A61G 13/02; A61G 13/08; A61G 2203/16; A61B 34/25; A61B 34/30
See application file for complete search history.

(56) References Cited

U.S. PATENT DOCUMENTS

| | | | |
|---|---|---|---|
| 8,508,340 B2 | 8/2013 | Sanchez Sanchez et al. | |
| 2009/0058598 A1* | 3/2009 | Sanchez Sanchez ... | G06F 21/32 340/5.83 |
| 2013/0096575 A1* | 4/2013 | Olson .................... | A61B 34/76 606/130 |
| 2013/0096701 A1* | 4/2013 | Suorajaervi ............ | A61G 13/08 700/83 |
| 2015/0085986 A1* | 3/2015 | Dinse ...................... | A61B 6/10 378/98 |
| 2016/0028874 A1 | 1/2016 | Mankopf et al. | |
| 2017/0080232 A1* | 3/2017 | Torgerson .......... | A61N 1/37247 |
| 2017/0140169 A1 | 5/2017 | Boger et al. | |
| 2019/0121524 A1* | 4/2019 | Hakansson ......... | G06F 3/04883 |

FOREIGN PATENT DOCUMENTS

DE       102013100428 A1     7/2014

OTHER PUBLICATIONS

European Search Report for European Application No. 20190369.7, dated Dec. 10, 2020.
German Search Report (Including Translation) for German Patent Application No. 10 2019 122 868.9, dated Mar. 27, 2020.

* cited by examiner

*Primary Examiner* — Alex Olshannikov
(74) *Attorney, Agent, or Firm* — Jason H. Vick; Sheridan Ross, PC

(57) ABSTRACT

A system and method for safely controlling a device, such as a medical device, via an input unit using a verification unit, wherein the input unit communicates with the verification unit via a communication channel is disclosed.

20 Claims, 3 Drawing Sheets

SAFE CONTROL METHOD AND SYSTEM

CROSS-REFERENCE TO RELATED APPLICATIONS

This application claims priority from German patent application DE 10 2019 122 868.9, filed on Aug. 26, 2019. The entire contents of this priority application are incorporated herein by reference.

BACKGROUND

The present disclosure relates to a method for the safe control of a medical device via an input unit using a verification unit, the input unit communicating with the verification unit via a communication channel. The disclosure further relates to a system with at least one processor and at least one memory, wherein the at least one memory contains instructions to carry out a method for safe control.

Medical equipment in an operating room usually comprises a control panel that is attached to the medical equipment or is permanently connected to the medical equipment. This ensures that the assignment between the control unit and the medical device is unambiguous and that control signals from the control unit actually only reach the corresponding medical device.

Today's operating rooms have an extensive network structure, whether wired or wireless, which makes it possible to control medical equipment with a control panel that is connected to the medical device via the network. This allows great flexibility in the arrangement of the control panel and it is possible to control a medical device using several control panels.

However, the network structure means that the safety requirements demanded in the field of medical devices can no longer be guaranteed without taking further measures. In order to guarantee the necessary safety, a separate enabling switch is assigned to an operating unit, which communicates with the medical device via a logically and physically separate signal path. When the medical device receives a control command from the control unit, the control command is only executed if the enable switch of this control unit is actuated at the same time. This ensures that a command that arrives at the medical device but was not sent by the corresponding control unit is not executed by the medical device.

Such a solution is reliable and may in principle be used with any medical device and control unit. However, in order to achieve the necessary safety, in particular safety class C according to the IEC 62304 standard, it is necessary to connect the enable switch to the medical device via the aforementioned signal path which is separate from the network.

SUMMARY OF THE DISCLOSURE

It is an object to provide a method for safe control as well as a corresponding system, in which the safety required for medical devices may be guaranteed even without a separate enabling switch.

According to a first aspect, there is provided a method for safely controlling a medical device via an input unit using a verification unit, the input unit communicating with the verification unit via a communication channel, the method comprising the steps of first detecting, by the input unit, of a first actuation at a first actuation point within a release area on the input unit, wherein the first actuation is a touch and a maintaining of the touch, first sending, from the input unit to the verification unit, of a request for unambiguous context information that establishes an unambiguous association between the actuation on the input unit and the verification unit, generating, by the verification unit, the context information, second sending, by the verification unit to the input unit, of the context information, second detecting, by the input unit, of a second actuation that follows the first actuation while continuously maintaining the touch, the second actuation being a movement from the first actuation point to a second actuation point within a control area on the input unit while continuously holding the touch, and controlling the medical device with the following repetitive steps:

third detecting, by said input unit, of a third actuation, said third actuation being a displacement within said control area while continuously holding said touch, third sending, from the input unit to the verification unit, of a control message comprising a control command, identification information and displacement information, wherein the control command is associated with the control area, the identification information comprises the context information or an information derived from the context information, and the displacement information comprises information in which the length and direction of the displacement is contained or may be determined therefrom, first checking, by the verification unit, whether the displacement information of at least a subset of the third actuations performed shows that the displacement on the input unit follows a predetermined shape, second checking, by the verification unit, whether the identification information corresponds to the context information, and fourth sending, by the verification unit to the medical device, of the control command or a command derived from the control command when the first checking and the second checking have been completed positively.

According to another aspect, there is provided a method for safely controlling a medical device via an input device using a verification system, the input device communicating with the verification system via a communication channel, the method comprising the steps of first detecting, by the input device, a first actuation at a first actuation point within a release area on the input device, wherein the first actuation is a touch and a maintaining of the touch, first sending, from the input device to the verification system, a request for unambiguous context information that establishes an unambiguous association between the actuation on the input device and the verification system, generating, by the verification system, the context information, second sending, by the verification system to the input device, the context information, second detecting, by the input device, a second actuation that follows the first actuation while continuously maintaining the touch with the input device, the second actuation being a movement from the first actuation point to a second actuation point within a control area on the input device while continuously holding the touch, and controlling the medical device with the following repetitive steps:

third detecting, by said input device, a third actuation, said third actuation being a displacement within said control area while continuously holding said touch, third sending, from the input device to the verification system, a control message comprising a control command, identification information and displacement information, wherein the control command is associated with the control area, the identification information comprises the context information or information derived from the context information, and the displacement information comprises information in which the length and direction of the displacement is contained or may be determined therefrom, first checking, by the verification system, whether the displacement information of at least a subset of the third actuations performed shows that the displacement on the input unit follows a predetermined shape, second checking, by the verification system, whether the identification information corresponds to the context information, and fourth sending, by the verification system to the medical device, the control command or a command derived from the control command when the first checking and the second checking have been completed positively.

The above aspect wherein the input device is a touchscreen and the verification system includes a processor, memory and instructions stored on the memory that perform the associated functions.

The above aspect wherein the first and second actuation require a constant contact with the input device, and/or the constant contact is via a finger of a user.

The above aspect wherein the first and second actuation require a constant or continuous contact with the touchscreen, and/or the constant contact is via a stylus.

One of the special features of this method is that in a first step, before a control command is generated at all, an unambiguous connection is established between the input unit and the medical device. This is done using the context information mentioned above. This context information, which is generated by the verification unit, enables the verification unit to unambiguously assign a control message, and thus a control command, to the input unit in the further course of the method. In addition, the input unit may identify itself to the verification unit by means of the identification information, which either comprises this context information or comprises derived information that unambiguously identifies the context information.

The term 'unambiguous' as used in this application covers, on the one hand, mathematically exact unambiguity. On the other hand, in the context of disclosure, such information should also be understood as unambiguous if it cannot be guessed or may only be determined by an impracticable number of attempts by trial and error. For example, the identification information could have a checksum of the context information and not the context information itself. If, for example, a checksum method is used which has over a billion, a trillion or more possibilities of the checksum, the assignment of the identification information to the context information should still be understood as unambiguous, since it is not practicable to guess the correct checksum by chance without actually knowing the context information.

Thus, the generation of the context information by the verification unit, the sending of the context information to the input unit and the subsequent sending of the identification information from the input unit to the verification unit ensures that only this unambiguous assignment is allowed for controlling the medical device.

It is also ensured that the unambiguous assignment may only be actively created by the user. This is because it requires the user to enter data at the input unit in a special area of the input unit, namely the release area. Only then does the input unit send the request for the context information at all.

Accidental or incorrect actuation of the input unit is then prevented by the requirement for a second press. This second actuation requires the user to move his finger, for example, from the first actuation point in the release area to a second actuation point within the control area, while continuously touching it. If this second actuation does not take place, the method continues to wait for the second actuation, at least for a predetermined time.

If the touch ends, even if it is only interrupted for a short time, the process may jump back to an initial state. The express shifting of the actuation point on the input unit from the enable area to the control area may only be randomly reproduced with a low probability. This ensures that the user actually wants to control the medical device via the input unit.

The actual control of the medical device via the input unit also ensures that the control is purposefully wanted by the user and is carried out undoubtedly and exclusively via the unambiguously assigned input unit. This is done by means of two independent checks, both of which must be completed positively in order for the medical device to be actually controlled.

On the one hand, it is checked whether a user actuation within the control area of the input unit follows a predefined form. In some exemplary embodiments, following the predetermined shape requires as frequent a change as possible in the length and/or direction of the individual pieces of displacement required to follow the shape. For example, the user draws a circle(s), rectangle(s), a back and forth pattern, and/or other predefined shape or pattern on the input device, and this predefined shape or pattern is correlated to a library of stored pre-defined shapes or patterns. This detected shape or pattern is then correlated to a corresponding control function for control of some aspect of equipment.

Although it is in principle possible to use a very simple form, such as a straight line, it may be difficult to distinguish an actual smooth motion, i.e. displacements that always have the same length and direction, from a situation where a frozen value of length and direction is repeatedly sent due to a system error. If, on the other hand, the shape is generated with many and possibly continuous changes of direction, frozen values of length and direction of the displacement may be recognized quickly.

The wording that a command is derived from the control command shall be understood to mean that it is not necessary that the verification unit exactly matches the control command sent by the input unit. Thus, it is also possible that the verification unit receives a control command in a certain format or with a certain information, but from this a command must be derived which corresponds to the input format or input information expected by the medical device.

It should be noted that the input unit only sends the displacement information, but does not exclusively check by itself whether the displacement within the control area by the user follows the pre-determined form. For example, if the input unit would simply tell by means of a bit whether the displacement follows the pre-determined form, the flip of a bit on the sending path could lead to an erroneous conclusion at the verification unit. Instead, the verification unit evaluates the displacement information to check the shape of the displacement on the input unit.

Basically all displacement information from all third actuations may be considered. However, it is usually sufficient to evaluate only a subset of the third actuations, especially if the third actuations are carried out in a very narrow time frame. Furthermore, it may be helpful to disregard certain displacement information, for example if the user lets the actuation rest for a short time, e.g. for a period of up to several hundred milliseconds.

The displacement information may be configured in many different ways. For example, the displacement information may directly contain the length and direction of the third actuation. The displacement information may also transmit the coordinates of the current touch point. Thus, knowing the last touch point, the length and direction of the third actuation may be determined. In addition, a starting position of the displacement may be transmitted in order to carry out further checks and plausibility considerations.

Furthermore, the second check is also carried out, which checks whether the identification information corresponds to the context information. The purpose of this check is to determine whether the sender of the identification information is in possession of the context information. If the identification information comprises the context information or is the same as the context information, this determination is particularly easy. However, it may well be sufficient for the identification information to contain only parts of the context information, provided that it is ensured that knowledge of the context information is not faked in a practicable way.

The identification information may also contain information derived from the context information, such as the checksum explained above. Since it is checked at least periodically or, in some exemplary embodiments, continuously, whether the identification information in the control message corresponds to the context information, it is continuously ensured that control commands are only accepted in the context of the unambiguous assignment between the input unit and the verification unit.

Furthermore, since both the unambiguous start of the control process and the continuous desire for active control by the user are checked, safe control is ensured.

It should be noted that actuation, touch, movement and holding may be haptic, i.e. in physical touch with the input unit, as in the case of a touch screen, or virtual, as in the case of virtual reality glasses, when the user touches, from his perspective, a virtual surface.

Due to the proposed concept, the process is so safe that it may meet safety class C according to the IEC 62304 standard. Regulatory requirements from abroad may also be met, see e.g. "General Principles of Software Validation", available at https://www.fda.gov/regulatory-information/search-fda-guidance-documents/general-principles-software-validation. This means, among other things, that the process may be used even with the highest safety requirements.

In an exemplary embodiment, the respective subsequent steps of the method will not be carried out if the touch is terminated during the execution of the method.

In this way it is ensured that no control can take place if the touch is interrupted, or that a started control is terminated.

In another exemplary embodiment, the method will continue with the first detecting if the touch is terminated during the execution of the method.

In this way it is ensured that the process returns to a defined initial state in case of an interrupted touch and thus no control can take place or a started control is terminated.

In another exemplary embodiment, the verification unit comprises an instruction processor and a verification processor and uses the instruction processor to provide the control instruction or the instruction derived from the control instruction for the fourth sending and uses the verification processor to enable the fourth sending.

This embodiment is particularly safe, since on the one hand the provision of the control command and on the other hand the release of the control command, i.e. that the control command can actually be sent, is carried out by means of two different physical components. Since the verification processor may then be configured very simply and may thus be cost-effectively configured for a high safety class, the required safety of the verification unit may be achieved cost-effectively overall.

In another exemplary embodiment, the context information comprises a device identification of the verification unit.

In this way it may be checked during execution of the method whether the identification information sent by the input unit is actually intended for the verification unit. This check may also be carried out via an additional element which is independent of both the input unit and the verification unit. Alternatively or additionally, it is possible that the context information comprises a device identification of the input unit.

In another exemplary embodiment, the context information comprises at least one element selected from a group including one or more of: time information, session information, sequence information and start information.

This embodiment allows one or more further checks to ensure that a control command is only pre-determined in the context of the unambiguous mapping between the input device and the verification unit. The plausibility of control messages may also be checked. For example, the time information may be used to check whether the control messages arrive in the correct time sequence, whether the distances in time between the control messages do not exceed a maximum distance, and whether the runtime of the control message from the input device to the verification unit does not exceed a maximum value.

The session information may be used to check whether the control message is in the context of the last first entry or whether an older context information is transmitted that should no longer be regarded as valid. The sequence information allows to check whether the control messages arrive in the correct sequence or allows to put asynchronous incoming control messages in the correct sequence. The start information, also known as seed information, provides a specific start value that cannot be determined by randomly trying in a practical way. For example, the start information may be a randomly generated number, especially a large number. If one of these checks fails, the received control message may be discarded or the control may be aborted and the method continued with the step of first detecting.

In another exemplary embodiment, the pre-determined shape is an oval shape, an ellipse shape or a circle shape.

This embodiment results in a particularly large number of changes in the direction of movement in the course of the mold. Thus, it may be quickly detected if the control message contains frozen displacement information which only seems to indicate a third actuation.

In another exemplary embodiment, the communication channel is exactly one physical and/or one logical channel, and in particular the control command is transmitted as exactly one message.

This embodiment may make it unnecessary to use multiple physical and/or logical channels. Furthermore, it is especially not necessary to send the control command in several messages. This allows a simplified structure for the connection between the input unit and the verification unit.

In another exemplary embodiment, the method is continued with the first detecting if the displacement information is identical or repeated within a pre-determined tolerance range.

As explained above, for some exemplary embodiments, the method is carried out in such a way that a periodic or continuous change of the control message and in particular of the displacement information may be expected. In particular, a user will not succeed in executing a movement in such a way that the displacement information is identical or repeated. Depending on the embodiment, a tolerance range may also be defined within which a displacement information should still be considered as identical. This means that if an identical or repeated displacement information is detected, it is to be assumed that the actuation is not performed by a user but is generated in some other way, for example by means of a so-called replay. In such a state, control messages, in some exemplary embodiments, may be discarded and/or the control may be aborted and/or the process may be continued with the first detecting.

According to a second aspect, there is provided a system having at least one processor and at least one memory, the at least one memory containing instructions which, when executed by the at least one processor, cause the at least one processor to perform the previously described method.

In an exemplary embodiment, the at least one processor comprises an instruction processor and a verification processor, wherein the verification processor is configured for first and second verification and release of the control instruction or the instruction derived from the control instruction, and the instruction processor is configured to provide the control instruction or the instruction derived from the control instruction.

As already explained above, this embodiment is particularly safe, since on the one hand the provision of the control command and on the other hand the release of the control command, i.e. that the control command may actually be sent, is done by means of two different components. Since the verification processor may then be configured very simply and may thus be cost-effectively configured for a high safety class, the required safety of the verification unit may be achieved cost-effectively overall.

In another exemplary embodiment, the input unit comprises a touch screen or gesture detecting unit, especially in combination with virtual reality glasses.

This embodiment enables the system to be implemented both on the basis of an actual touch and on the basis of a virtual touch. This is particularly interesting with regard to the increasing use of virtual reality glasses, since the user may then control the system safely without the need for a haptic touch of a surface.

In another exemplary embodiment, the input unit is configured for input by hand and/or finger of a user.

This type of input is particularly simple and intuitive.

In another exemplary embodiment, the medical device is an operating table and/or other device(s) within the operating theatre.

This embodiment may be viewed as advantageous because the continuous third actuation within the control area is intuitively carried out exactly as long as the operating table is to be moved. In addition, it is easy to provide at least two control areas on the input unit, which generate different control commands. Thus, different elements of the operating table and/or different directions of movement of an element of the operating table may be controlled.

It goes without saying that the features mentioned above and those to be explained below may be used not only in the combination indicated in each case, but also in other combinations or in isolation, without leaving the spirit and scope of the present disclosure.

BRIEF DESCRIPTION OF THE DRAWINGS

Exemplary embodiments are shown in the drawing and are explained in more detail in the following description. In the figures.

DESCRIPTION OF EXEMPLARY EMBODIMENTS

Figure 1:
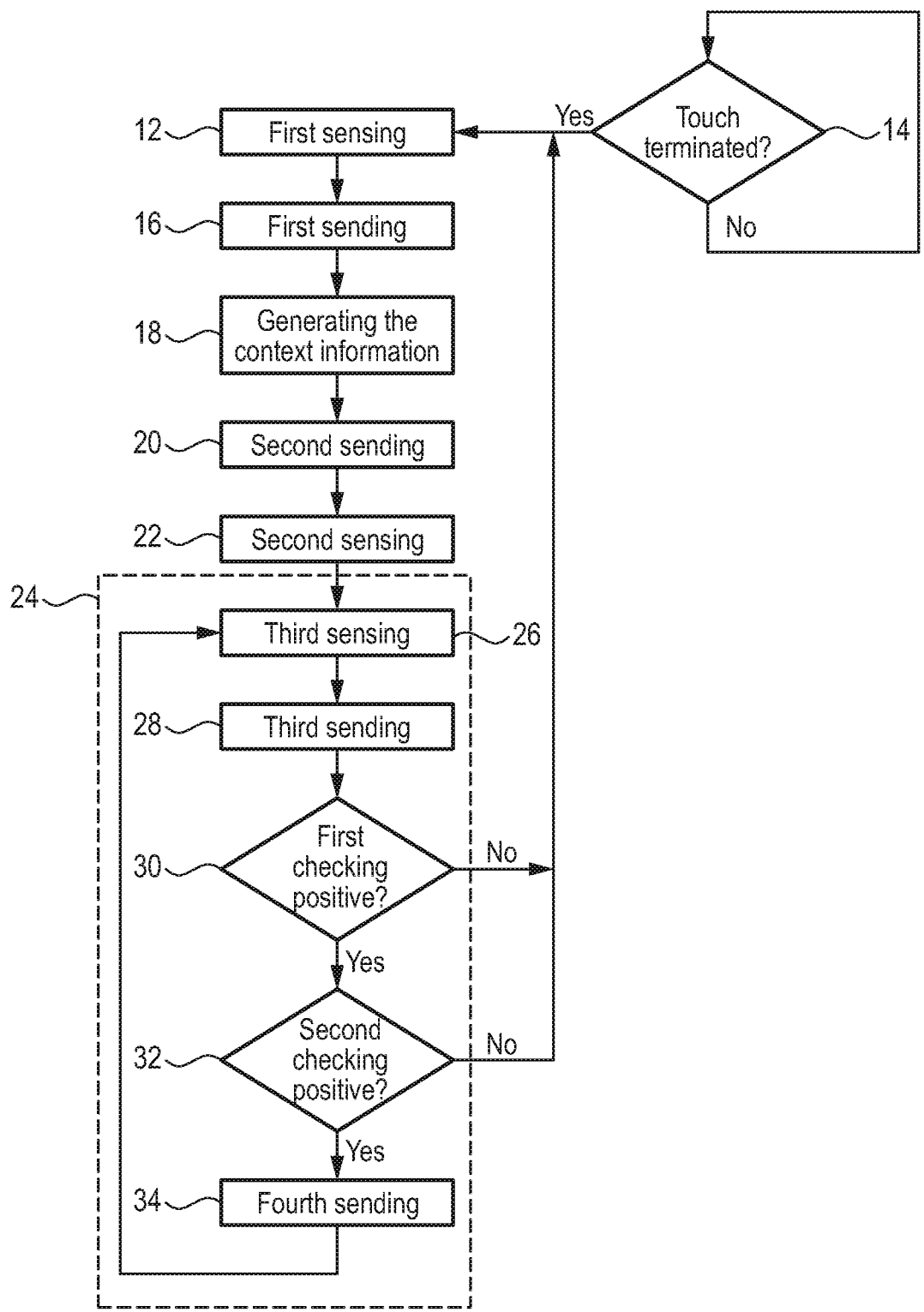
FIG. 1 shows an embodiment of a method for safely controlling of a medical device via an input unit.
Figure 2:
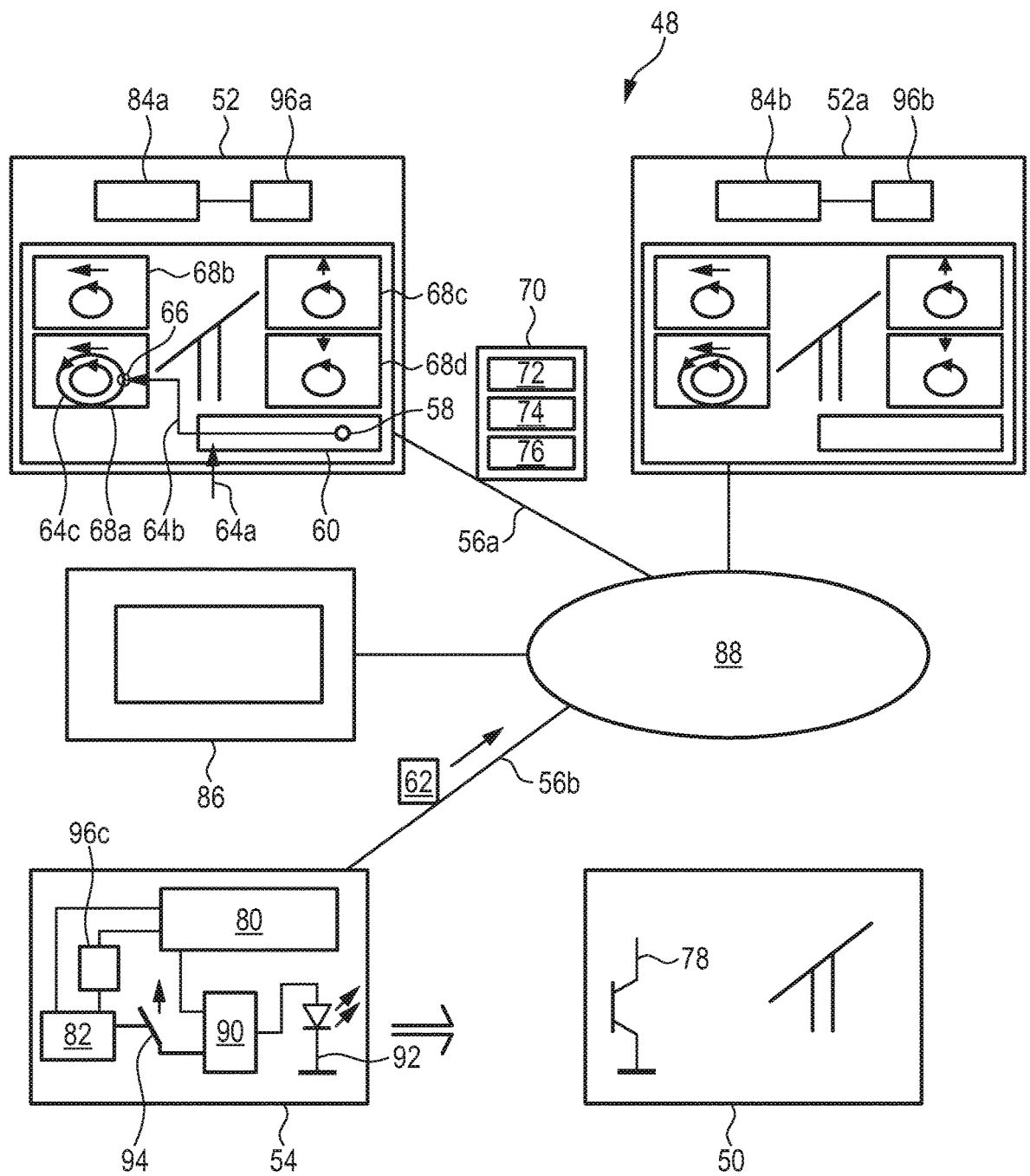
FIG. 2 shows an embodiment of a system with at least one processor executing a method for safely controlling a medical device via an input unit.
Figure 3:
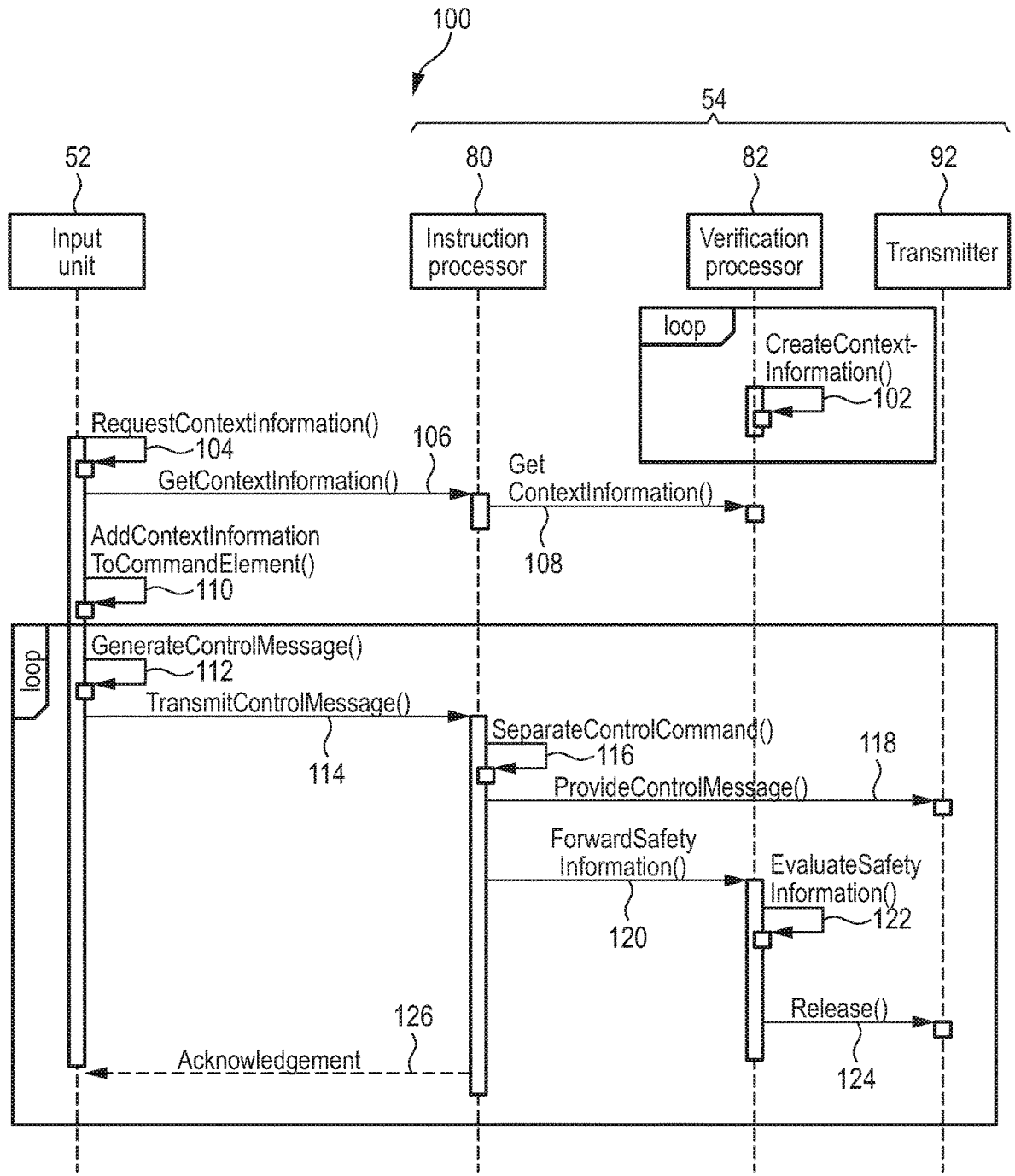
FIG. 3 shows an embodiment of a history of commands and messages in a method of safely controlling a medical device via an input unit.

The following explanations are based on the overall context of FIGS. 1 to 3.

FIG. 1 shows a method for the safe control of a medical device 50 via an input unit 52 using a verification unit 54, where the input unit 52 communicates with the verification unit 54 via a communication channel 56a, 56b, such as an Ethernet connection, optical connection, wired connection, wireless connection, or the like.

The method comprises a first detecting 12, by the input unit 52, of a first actuation at a first actuation point 58 within a release area 60 on the input unit 52. The first actuation 64a is a touch and a continuous holding of the touch. For example, when the input unit 52 is a touchscreen and the touch is performed by a finger, the finger is kept in constant contact with the touchscreen.

It is symbolically shown in step 14 that method 10 is continued with the first detecting 12 if the touch is terminated. In this configuration, this check takes place in the background and is therefore not assigned to a specific point in the process. In other embodiments, the process is stopped when the touch is ended and/or the process is set to a defined initial state and/or the user is informed of the end of the touch by a message, for example on the touchscreen.

In the step of the first sending 16, the input unit 52 sends a request 106 to the verification unit 54 to receive from there an unambiguous context information 62. The context information 62 establishes an unambiguous assignment between the actuation on the input unit 52 and the verification unit 54.

Upon request 106 by input unit 52, verification unit 54 generates the context information in step 18.

When the context information 62 is generated, it is sent by a second sending 20 from the verification unit 54 to the input unit 52.

Then a second detecting 22, by the input unit 52, follows a second actuation 64b. The second actuation 64b is a movement from the first actuation point 58 to a second actuation point 66 within a control area 68a on the input unit 52. This movement takes place while the touch is continuously held. It should be remembered here, see step 14, that method 10 continues with the first detecting 12 if the touch is ended. If the second actuation 64b has been detected, step 24 now controls the medical device 50 with repetitive steps, which are explained in more detail below. Again, it is important to remember that method 10 continues with the first detecting 12 if the touch is ended 14.

First the input unit 52 performs a third detecting 26 of a third actuation 64c. The third actuation 64c is a displacement within the control area 68a with continuous holding of the touch.

This is followed by a third sending 28, from the input unit 52 to the verification unit 54, of a control message 70, which comprises a control command 72, identification information 74 and displacement information 76. Control command 72 is assigned to control area 68a. In the execution shown here, for example, the further control area 68b sends a further control command that is different from control command 72.

The identification information 74 comprises the context information 62 or an information derived from the context information 62. This information may be obtained, for example, by shortening or extending context information 62 or be the result of a calculation, such as a checksum, based on context information 62. The displacement information 76 contains information that contains or may be determined from the length and direction of the displacement. The temporal resolution for determining the displacement is selected in such a way that the shape of the movement performed by the user on control area 68a may be determined from a plurality of displacement information 76.

During a first checking 30, by the verification unit 54, it is checked whether the displacement information received so far or received last from at least a subset of the third actuations performed shows that the displacement on the input unit 52 follows a predetermined form. If, for example, an arc may be recognized by looking at the individual, usually short segments of the third actuation, a circular shape may be concluded from this.

During a second checking 32, the verification unit 54 checks whether the identification information 74 corresponds to the context information 62. In particular, it is to be checked that the identification information 74 was generated with knowledge of the context information 62 and was not generated by chance.

If the first checking 30 and the second checking 32 are completed positively, a fourth sending 34, by the verification unit 54, to the medical device 50, of the control command or a command derived from the control command, is performed. The medical device 50 is now actually controlled. This may mean, for example, that the medical device 50 or part of it is displaced.

In accordance with one exemplary embodiment, verification unit does the monitoring of the continuous touch and performs the "reset" in the event of, for example, loss of touch. However, the input unit can also perform the reset, for example, upon the detection of a loss of contact with the finger of a user. As part of the safety mechanism of an aspect of the disclosed technology, when the verification unit detects any kind of abnormality, this includes a release of the touch, the verification unit resets/cancels/deletes the context information. This means that any further data sent by the input unit will be disregarded due to the lack of valid context information. The input unit may or may not be informed of this, however, the input unit will not be able to perform any control until the process restarts. In one configuration, the verification unit will inform the input unit, so a graphical or audible warning or information can be provided to the user. The correct operation of the medical device is ensured through the verification unit detecting an abnormality and transitioning to a waiting state for a touch in the release area that will start the whole process over again by generating valid context information.

This means a) the input unit may detect an interrupted touch and inform the user, however, this is optional, and b) the verification unit may detect an interrupted touch and inform the user, however, this is also optional. Rather, it is any abnormality detected by the verification unit that resets/cancels/deletes the context information, thus no longer accepting that context information, and consequently requiring the user to start again in the release area which triggers the generation of new context information and allows a subsequent continuous contact with the touchscreen to generate a new control command.

In the embodiment of method 10 shown here, it may be seen that either a negative result of the first check 30, see the NO path, or a negative result of the second check 32, see the NO path, will result in a return to the first detecting 12. However, it is also possible to jump to the third detecting 26 if the result is negative, and only return to the first detecting 12 after several negative checks.

FIG. 2 shows a system 48 with an instruction processor 80, a verification processor 82, a first input device processor 84a in the input unit 52 and a second input device processor 84b in another input unit 52a. A central controller 86 of the system 48 is also shown. The input unit 52 is connected to the verification unit 54 via a network 88. This may be the KARL STORZ® Communication Bus (SCB), for example.

The medical device 50 here is an operating table and comprises a receiver 78. The verification unit 54 comprises a logic circuit 90 which only sends a command via the transmitter 92, in particular through infrared sending, if both a control command or a command derived from the control command has been provided by the command processor 80 for the fourth sending 34 and the verification processor 82 enables the fourth sending 34 by means of the symbolically represented switch 94. The system 48 further comprises a memory composed of a first memory 96a in the input unit 52, a second memory 96b in the further input unit 52a, and a third memory 96c in the verification unit 54. In the embodiment shown here, the first memory 96a and the third memory 96c contain instructions which, when executed by the at least one processor, cause the at least one processor to execute a method 10 as previously described. One or more of the memories can include, for example, a Javascript, instructions, algorithms, or comparable functionality that performs one or more of the functions described herein.

The continuous touch can be accomplished, for example, using image processing techniques. If the user draws a circle with their finger, the user creates at the user interface on the touchscreen many X/Y screen coordinates. These coordinates could be queued into a graphic track element such as a path or shape element (see for example Scalable Vector Graphics (SVG) paths and SVG elements). With an image processing library the system can check the received inputs to determine if they correspond to one of the pre-defined shapes/patterns using techniques/commands such as: IsLine( . . . ), IsRectangle( . . . ) or even IsCircle( . . . ) or IsEllipse( . . . ). If the result is positive, the user input has been detected and correlated to drawing a ellipse or circle, etc., within the user interface element.

Image processing libraries which contain representations of stored shapes/patterns contain information for how a rectangle is to be drawn. For example, the system could look for a first number of vectors pointing substantially in a first direction and a second number of vectors pointing substantially in a second direction, where the first and second directions are substantially perpendicular to each other. Then, the second vs. a third set, the third vs. a fourth, etc. If the system was looking to detect a square, then the system determines whether the distances between that "90° changes in direction" occur at substantially equal distances. Or, for a circle, the system would expect that, if fixing the middle point of the vectors to a fixed point, the system would see that the sequence of vectors rotates about that fixed point, one of either clockwise or counter-clockwise. In general, one aspect uses an image processing library to detect if the user drawn gesture was a circle or ellipse or any other pre-defined shape or pattern.

It is to further be appreciated that the system can include the ability to recognize multiple finger gestures. Similar to the single finger example, the multiple finger gestures would need to include a continuous touch and would need to be repeated in a loop, but do not have to be not exactly identical like moving two of your fingers together and away. This gesture is similar but passes different X/Y coordinates. Similarly, one finger could be detected as making circles in a clockwise direction, while another finger could be detected ad making circles in a counter-clockwise direction. These movements could be correlated to a single command or multiple commends, such as a complex command (e.g., move the operating table up and to the left). Similar to other embodiments, ongoing user interaction is active until the user releases the touch from the input device.

One benefit of the gesture recognition described herein is safety—and the ignoring of gesture which could be produced by system malfunction. This is done by drawing continuous figures like a circle at the input device. While many circles are possible, these are not typically drawn by passing over exactly the same last circle coordinates which adds to the safety. In case of touchscreen input device, the finger gesture movement is 2D—X/Y coordinates. In case of gesture control by VR data glasses with gesture control or Microsoft® Kinect or Intel® Real Sense, or comparable augment reality or virtual reality systems, 3D gestures are possible with X/Y/Z coordinates and corresponding 3D shapes in the library.

FIG. 3 shows an example of the course 100 of commands and messages on and between the different elements. First of all, the command CreateContextInformation( ) 102 is pointed out. This is permanently executed by the verification processor 82, so that periodically, e.g. at intervals of several hundred milliseconds, especially 200 ms to 800 ms, a new context information 62 is always generated.

In input unit 52, the command RequestContextInformation( ) 104 is executed first. Then the message GetContextInformation( ) 106 is sent to the command processor 80, which is connected to the communication channel 56a, 56b. It is also possible to send the message directly to the verification processor 82, but this would increase the complexity of the verification processor 82. By means of the message GetContextInformation( ) 108, the command processor 80 requests context information 62 from the verification processor 82, which is then sent back (not shown) to the input unit 52 via the command processor 80.

With the function AddContextInformationToCommandElement( ) 110 the context information 62 is linked to the control area 68a.

The following commands and messages are executed or sent within a loop.

First, the control message 70 is generated using the command GenerateControlMessage( ) 112. Control message 70 is sent to the command processor 80 using the message TransmitControlMessage( ) 114. There, the command SeparateControlCommand( ) 116 is used to separate the control command 72 from the other elements of the control message 70, i.e. from the identification information 74 and the displacement information 76.

By means of the message ProvideControlCommand( ) 118 to the transmitter 92 the control command 72 or a command derived from the control command 72 is prepared for sending. By means of the message ForwardSafetyInformation( ), the identification information 74 and the displacement information 76 are forwarded to the verification processor 82. Using the EvaluateSafetyInformation( ) 122 command, the first checking 30 and the second checking 32 are performed. If the first checking 30 and the second checking 32 have been completed positively, the message Release( ) 124 is used to release to the transmitter 92 that the provided control command 72 may be sent. Optionally, message 126 may be used to acknowledge the successful or unsuccessful execution of control command 72 from command processor 82 to input unit 52.

The invention claimed is:

1. A method adapted for safely controlling a medical device via an input unit using a verification unit, the input unit communicating with the verification unit via a communication channel, the method comprising:
  first detecting, by the input unit, of a first actuation at a first actuation point within a release area on the input unit, wherein the first actuation is a touch and a maintaining of the touch,
  first sending, from the input unit to the verification unit, of a request for unambiguous context information that establishes an unambiguous association between the actuation on the input unit and the verification unit,
  generating, by the verification unit, the context information,
  second sending, by the verification unit to the input unit, of the context information, wherein the context information is unique to the input unit,
  second detecting, by the input unit, of a second actuation that follows the first actuation while continuously maintaining the touch, the second actuation being a movement from the first actuation point to a second actuation point within a control area on the input unit while continuously holding the touch, wherein the control area is distinct from the release area, and
  controlling the medical device with the following repetitive steps for subsequent actuation while continuously holding said touch:
    detecting, by said input unit, of a next actuation, said next actuation being a displacement within said control area while continuously holding said touch,
    sending, from the input unit to the verification unit, of a control message comprising a control command, identification information and displacement information, wherein the control command is associated with the control area, the identification information comprises one of the context information or an information derived from the context information, and the displacement information comprises information in which the length and direction of the displacement is contained or may be determined therefrom,
    checking, by the verification unit, whether the displacement information of at least a subset of the next actuations performed shows that the displacement on the input unit follows a predetermined shape, checking, by the verification unit, whether the identification information corresponds to the context information, and sending, by the verification unit to the medical device for the subsequent actuation of one of the control command or a command derived from the control command when the checking steps have been completed positively.

2. The method of claim 1, whereby the respective subsequent steps of the method are not carried out if the touch is terminated during the execution of the method.

3. The method of claim 1, wherein the method continues with the first detecting if the touch is terminated during the execution of the method.

4. The method of claim 1, wherein the verification unit comprises an instruction processor and a verification processor and provides with the instruction processor one of the control instruction or the instruction derived from the control instruction for the sending for the subsequent actuations and enables with the verification processor the sending for the subsequent actuations.

5. The method of claim 1, wherein the context information comprises a device identification of the verification unit.

6. The method of claim 1, wherein the context information comprises at least one element selected from a group consisting of time information, session information, sequence information and start information.

7. The method of claim 1, where the pre-determined shape is at least one of an oval shape, an ellipse shape or a circle shape.

8. The method of claim 1, wherein the communication channel is exactly one physical and/or one logical channel.

9. The method of claim 1, wherein the control command is sent as exactly one message.

10. The method of claim 1, wherein the method is continued with the first detecting if the displacement information is identical or repeated within a predetermined tolerance range.

11. A system comprising at least one processor and at least one memory, wherein the at least one memory contains instructions which, when executed by the at least one processor, cause the at least one processor to perform a method comprising:

first detecting, by the input unit, of a first actuation at a first actuation point within a release area on the input unit, wherein the first actuation is a touch and a maintaining of the touch, first sending, from the input unit to the verification unit, of a request for unambiguous context information that establishes an unambiguous association between the actuation on the input unit and the verification unit, generating, by the verification unit, the context information, second sending, by the verification unit to the input unit, of the context information, wherein the context information is unique to the input unit, second detecting, by the input unit, of a second actuation that follows the first actuation while continuously maintaining the touch, the second actuation being a movement from the first actuation point to a second actuation point within a control area on the input unit while continuously holding the touch, wherein the control area is distinct from the release area, and controlling the medical device with the following repetitive steps for subsequent actuation while continuously holding said touch:

detecting, by said input unit, of a next actuation, said next actuation being a displacement within said control area while continuously holding said touch, sending, from the input unit to the verification unit, of a control message comprising a control command, identification information and displacement information, wherein the control command is associated with the control area, the identification information comprises one of the context information or an information derived from the context information, and the displacement information comprises information in which the length and direction of the displacement is contained or may be determined therefrom, checking, by the verification unit, whether the displacement information of at least a subset of the next actuations performed shows that the displacement on the input unit follows a predetermined shape, checking, by the verification unit, whether the identification information corresponds to the context information, and sending, by the verification unit to the medical device for the subsequent actuations of one of the control command or a command derived from the control command when the checking steps have been completed positively.

12. The system of claim 11, wherein the at least one processor comprises an instruction processor and a verification processor, wherein the verification processor is configured for the checking steps and enabling one of the control instruction or the instruction derived from the control instruction, and the instruction processor is configured for providing one of the control instruction or the instruction derived from the control instruction.

13. The system of claim 11, wherein the input unit comprises one of a touch screen, a gesture detection unit or virtual reality glasses.

14. The system of claim 11, wherein the input unit is configured for input by means of a user's hand and/or finger.

15. The system of claim 11, wherein the medical device is an operating table.

16. A system comprising:

an input device configured to receive an input associated with a continuous user contact with the input device;

the input device configured to detect a first user input at a first actuation area within a release area within a user interface;

a verification processor configured to receive from the input device a request for context information that establishes an association between the actuation on the input device and the verification processor, and to send the context information to the input device, the context information being unique to the input unit, the input device further configured to detect a second user input between the first actuation area and a second actuation area within a control area within the user interface, wherein continuous contact with the user interface is maintained between the first user input and the second user input, and wherein the control area is distinct from the release area; and controlling a device with the following repetitive steps for subsequent actuations while continuously holding said touch:

the input device further configured to detect further user input corresponding to motion within the control area of the user interface and to send to the verification processor a control message comprising a control command, identification information and displacement information, wherein the control command is associated with the control area, the identification information comprises one or more of the context information and/or information derived from the context information, and the displacement information comprises information in which the length and direction of the displacement is contained or may be determined therefrom, the verification processor further configured to check whether the motion shows that the displacement on the input unit follows a predetermined shape, the verification processor further configured to check whether the identification information corresponds to the context information, and when the checks are confirmed for the subsequent actuations, the verification processor is further configured to send to the device a device control command.

17. The system of claim 16, wherein the input device is a touchscreen and the user input is 2D.

18. The system of claim 16, wherein the input device is a virtual reality or augmented reality system and the user input is multi-dimensional.

19. The system of claim 16, wherein the device is a medical device.

20. The system of claim 16, wherein continuous contact with the input device is maintained between the first user input, the second user input and the further user input.

* * * * *